United States Patent [19]

Buckberg et al.

[11] Patent Number: 5,609,571
[45] Date of Patent: Mar. 11, 1997

[54] APPARATUS AND METHOD OF CARDIOPLEGIA DELIVERY

[75] Inventors: Gerald D. Buckberg, Los Angeles; Russell A. Heimstaedt, Irvine; John M. Taylor, Trabuco Canyon, all of Calif.

[73] Assignee: Sorin Biomedical Inc.

[21] Appl. No.: 379,393

[22] Filed: Jan. 26, 1995

[51] Int. Cl.[6] ................................................. A61M 37/00
[52] U.S. Cl. .............................. 604/4; 604/53; 604/113; 604/122; 128/DIG. 3
[58] Field of Search ................................... 604/4–9, 113, 604/53, 122, 403, 406; 128/DIG. 3, DIG. 12; 422/44, 46

[56] References Cited

U.S. PATENT DOCUMENTS

| | | |
|---|---|---|
| 3,825,060 | 7/1974 | Heller et al. . |
| 4,065,264 | 12/1977 | Lewis . |
| 4,282,180 | 8/1981 | Raible . |
| 4,416,280 | 11/1983 | Carpenter et al. . |
| 4,427,009 | 1/1984 | Wells et al. . |
| 4,433,971 | 2/1984 | Lindsay et al. . |
| 4,512,163 | 4/1985 | Wells et al. . |
| 4,559,999 | 12/1985 | Servas et al. . |
| 4,568,330 | 2/1986 | Kajawski et al. . |
| 4,653,577 | 3/1987 | Noda . |
| 4,883,455 | 11/1989 | Leonard . |
| 5,282,783 | 2/1994 | Lindsay . |
| 5,322,500 | 6/1994 | Johnson et al. . |
| 5,358,481 | 10/1994 | Todd et al. . |
| 5,385,540 | 1/1995 | Abbott et al. . |
| 5,403,273 | 4/1995 | Lindsay . |
| 5,411,705 | 5/1995 | Thor et al. . |
| 5,423,749 | 6/1995 | Merte et al. . |

FOREIGN PATENT DOCUMENTS

PCT/US92/04028 5/1992 WIPO .

OTHER PUBLICATIONS

A Straight–Forward Approach To Cardioplegia Delivery (2 pages, 1985), Gish Biomedical, Inc.
All–Purpose Cardioplegia Heat Exchanger (5 pages, May 1987), Medtronic Eletromedics.
CardioPlegia Over Pressure Valve, (1 page), American Omni Medical, Inc.
The Creation of a Classic. A Precision Engineered Cardioplegia Delivery System, (12 pages, May 1993), Bard Cardiopulmonary Division.
K+ardia Cardioplegia Delivery System, (2 pages, 1993), Cobe Cardiovascular Inc.
New Approaches to Blood Cardioplegic Delivery to Reduce Hemodilution and Cardioplegic Overdose, Kai Ihnken, M.D., Kiyozo Morita, M.D., and Gerald D. Buckberg, M.D., J. Card. Surg., 1994; 9:26–36.
Presenting the Sorin BCD Avanced. The Complete Picture of Consistent Performance. (2 pages), Sorin Biomedical, Inc.
Scimed's MYOtherm Cardioplegia System (2 pages).
Single Pass Blood Cardioplegia Systems (2 pages, Oct. 1992), Gish Biomedical, Inc.
With the Monolyth, Superior Performance is a Matter of Course. (10 pages), Sorin Biomedical, Inc.

Primary Examiner—John D. Yasko
Assistant Examiner—Perry E. Van Oner
Attorney, Agent, or Firm—Popovich & Wiles, P.A.

[57] ABSTRACT

A cardioplegia delivery device and method of use for delivering warm or cold cardioplegia fluid to the heart of a patient. The delivery device includes an air chamber having a housing with an integral pressure relief valve for diversion of cardioplegia fluid if the fluid pressure within the housing exceeds a predetermined pressure. The air chamber includes a membrane and one-way valve located near the top of the housing for removal of air from the cardioplegia fluid. The delivery device may include an integral heat exchanger for controlling the temperature of the cardioplegia fluid.

13 Claims, 9 Drawing Sheets

APPARATUS AND METHOD OF CARDIOPLEGIA DELIVERY

Reference is made to our co-pending application, Ser. No. 08/381,690 filed on even date herewith entitled Cardioplegia Delivery System and Method For Convening From Warm Cardioplegia To Cold Cardioplegia which is hereby incorporated by reference.

FIELD OF THE INVENTION

This invention relates to apparatus and methods used in the administration of blood and cardioplegia solutions during cardiac surgery. More particularly, the invention is directed to a cardioplegia delivery deuce and method of its use which may be utilized to deliver either warm or cold cardioplegia fluids to the heart.

BACKGROUND OF THE INVENTION

During open hear surgery the blood of the patient is bypassed to an extracorporeal support system which supplies the pumping function of the heart and the oxygenation function of the lungs. This effectively isolates the heart enabling the surgeon to make the necessary repairs to the heart. During the surgery it is desirable to arrest the beating/pumping action of the heart. It is also important during the time that the heart is isolated from the blood supply circuit that the heart be protected from ischemia or lack of blood flow which can result in permanent damage to the heart.

It is well known that the heart may be protected during open hear surgery by utilizing a technique commonly known as cold cardioplegia. This involves administering to the hear a cooled cardioplegia fluid which may consist of a crystalloid chemical solution containing potassium and other additives or a mixture of the crystalloid solution with blood. Use of a cooled cardioplegia fluid comprising a mixture of oxygenated blood and crystalloid solution is known to be effective in keeping the heart arrested while at the same time keeping the heart oxygenated. The cardioplegia fluid is cooled by utilizing a cardioplegia delivery system which includes a heat exchanger.

In addition to the cold cardioplegia technique described above, some heart surgeons have more recently begun utilizing a technique called warm continuous blood cardioplegia. In this technique the cardioplegia fluid is not cooled and, consequently, it is not necessary to use a heat exchanger in the cardioplegia delivery system. This technique involves supplying a cardioplegia fluid mixture of warm oxygenated blood and cardioplegia solution throughout the cardiac surgery. This technique has gained acceptance among some surgeons as a safe and effective means of arresting and protecting the heart during surgery.

Whether warm cardioplegia or cold cardioplegia is prescribed by the physician, the manner of administration of the cardioplegia fluid during surgery is similar. Cardioplegia delivery systems include components which supply blood and cardioplegia solution, mix the desired ratio of blood/cardioplegia solution and then supply the mixture to the patient's heart. A specific ratio of oxygenated blood with cardioplegia solution containing potassium and other additives, is delivered to the coronary arteries. The term cardioplegia fluid, as used herein, shall mean any ratio of blood to cardioplegia solution and shall include 100% blood or 100% cardioplegia solution. Once the heart is arrested, the delivery system continues to supply the cardioplegia fluid to keep the heart arrested and to deliver oxygen to the myocardium. Pressures and temperatures are monitored to avoid damage to the heart. At the end of the bypass procedure, 100% blood is commonly administered to flush the cardioplegia solution out of the myocardium allowing the heart to be returned to its normal sinus rhythm.

During the process of cardioplegia delivery several problems can arise. First, air bubbles can be created in the cardioplegia fluid. Second, if a line is clamped during the procedure the cardioplegia delivery system may become over pressurized. Thus, it would be highly desirable to provide a cardioplegia delivery device which is able to eliminate air bubbles which are inadvertently admitted into the cardioplegia fluid. It would also be advantageous to provide a cardioplegia delivery device which is able to safely and efficiently react to over pressurization of the system without damaging the components of the system or resulting in loss of the patient's blood or cardioplegia solution.

SUMMARY OF THE INVENTION

In accordance with the present invention there is disclosed a blood cardioplegia delivery device. The device includes a housing having a fluid inlet port adapted to receive a cardioplegia fluid and a fluid outlet port in fluid communication with the inlet port. The delivery device further includes an air removal element located within the housing and a pressure relief valve incorporated into the housing. The pressure relief valve is adapted to divert the flow of cardioplegia fluid if the fluid pressure in the interior portion of the housing exceeds a selected or known fluid pressure based upon the design specifications of the pressure relief valve. The air removal element may include a membrane located at a top portion of the housing and a one-way valve located above the membrane. The one-way valve is adapted to allow air to flow from the housing through the membrane to the exterior of the housing when the air pressure in the air chamber exceeds a selected air pressure based upon the design specifications of the one-way valve. The membrane is adapted to allow air to flow through the membrane and to block fluid from flowing through the membrane under normal operating pressures of the device. The air removal element may further include a screen positioned in the fluid flow path between the fluid inlet and fluid outlet.

In a further embodiment, the delivery device may include a heat exchanger. The heat exchanger has a heat exchange fluid flow path lying between a heat exchange fluid inlet and a heat exchange fluid outlet. The heat exchanger includes a cardioplegia fluid flow path between a cardioplegia fluid inlet and a cardioplegia fluid outlet. The cardioplegia fluid outlet is connected to the fluid inlet port of the housing.

In a further embodiment the invention is a blood cardioplegia delivery device which comprises an air chamber having a housing defining an interior portion and having a fluid inlet port adapted to receive a cardioplegia fluid. The housing further has a fluid outlet adapted for delivery of the cardioplegia fluid to a patient. The device includes a membrane located at a top portion of the air chamber and a one-way valve located in the housing above the membrane. The one-way valve is adapted to allow air flow from the air chamber through the membrane to the exterior of the housing when the air pressure in the air chamber rises above a predetermined air pressure based upon the design specifications of the one-way valve. In one embodiment the predetermined air pressure may be 5 mmHg. The device includes a pressure relief valve which is incorporated into the housing as an integral portion thereof. The pressure relief valve is adapted to open so that cardioplegia fluid is diverted to flow out of the pressure relief valve when the fluid pressure in the interior portion of the housing rises above a predetermined fluid pressure based upon the design specifications of the pressure relief valve. In one embodiment the predetermined fluid pressure is 600 mmHg. The device further includes a heat exchanger connected to the housing of the air chamber for controlling the temperature of the cardioplegia fluid which is delivered to the patient. The device may further include a screen positioned in the housing in the fluid flow path between the fluid inlet and outlet.

In still a further embodiment the invention is a method of delivering cardioplegia fluid to the heart of a patient during open heart surgery. The method comprises providing an air chamber having a housing which includes a fluid inlet port adapted to receive the cardioplegia fluid and a fluid outlet port in fluid communication with the inlet port. The air chamber further includes an air removal element located within the housing and a pressure relief valve incorporated into the housing as an integral portion thereof. The pressure relief valve is adapted to divert fluid flow from the housing if the fluid pressure in the housing exceeds a selected fluid pressure based upon the design specifications of the pressure relief valve.

The method further includes connecting the fluid inlet port of the air chamber to a cardioplegia fluid source and connecting the fluid outlet port of the air chamber to cardioplegia tubing which is connected for infusion of the cardioplegia fluid to the heart of a patient. The method includes delivering the cardioplegia fluid from the cardioplegia source through the air chamber to the patient's heart.

In one embodiment the air removal element that is provided includes a membrane which may be located at a top portion of the air chamber and a one-way valve adapted to allow air to flow from the air chamber through the membrane to the exterior of the housing when the air pressure in the air chamber exceeds a selected air pressure based upon the design specifications of the one-way valve. The air removal element may further include a screen positioned within the fluid flow path between the fluid inlet and the fluid outlet. The method may further include adjusting the temperature of the cardioplegia fluid that is delivered to the patient's heart.

BRIEF DESCRIPTION OF THE DRAWINGS

The foregoing and other aspects of the present invention will be best appreciated with reference to the detailed description of the invention which follows when read in conjunction with the accompanying drawings wherein.

DETAILED DESCRIPTION OF THE INVENTION

The Cardioplegia System

Figure 1:
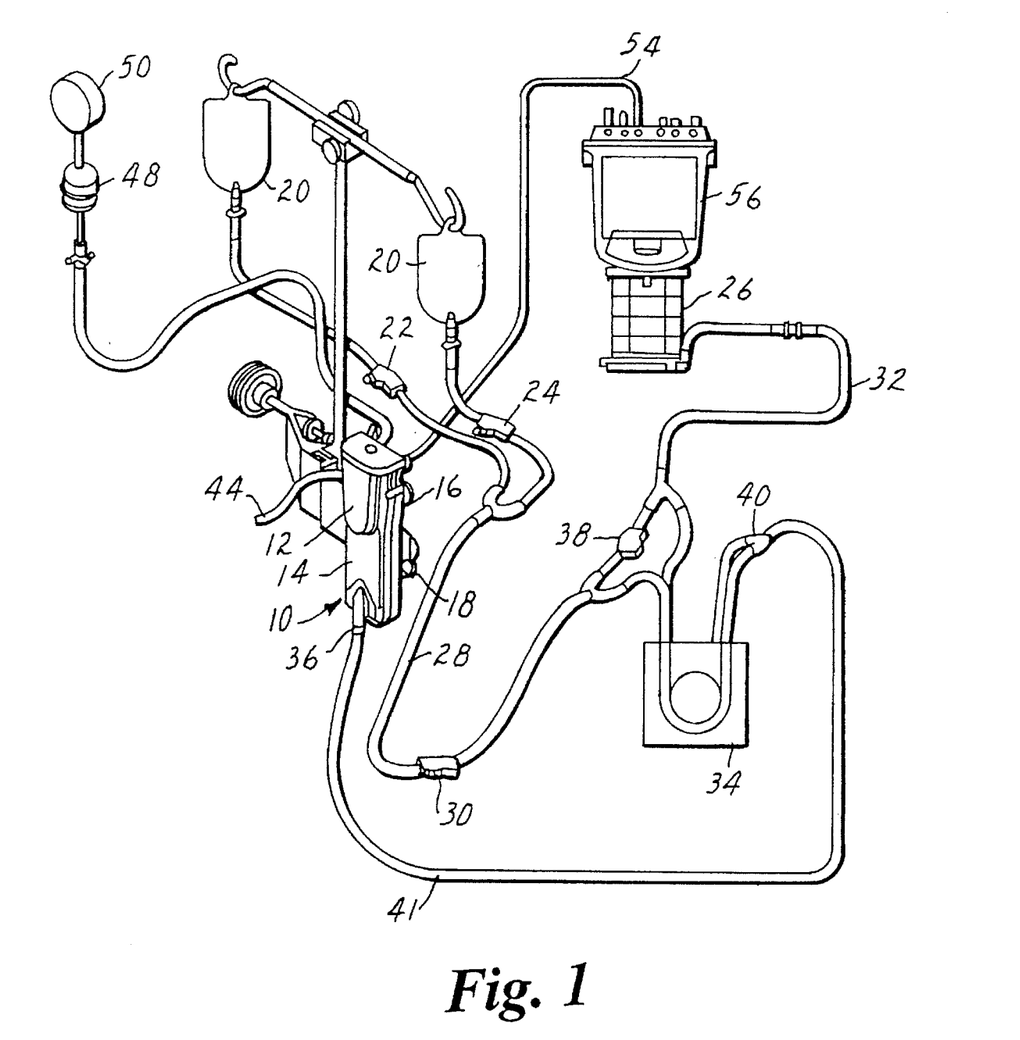
FIG. 1 is a schematic view of a cardioplegia delivery system which includes a cardioplegia delivery device in accordance with the present invention.
Figure 2:
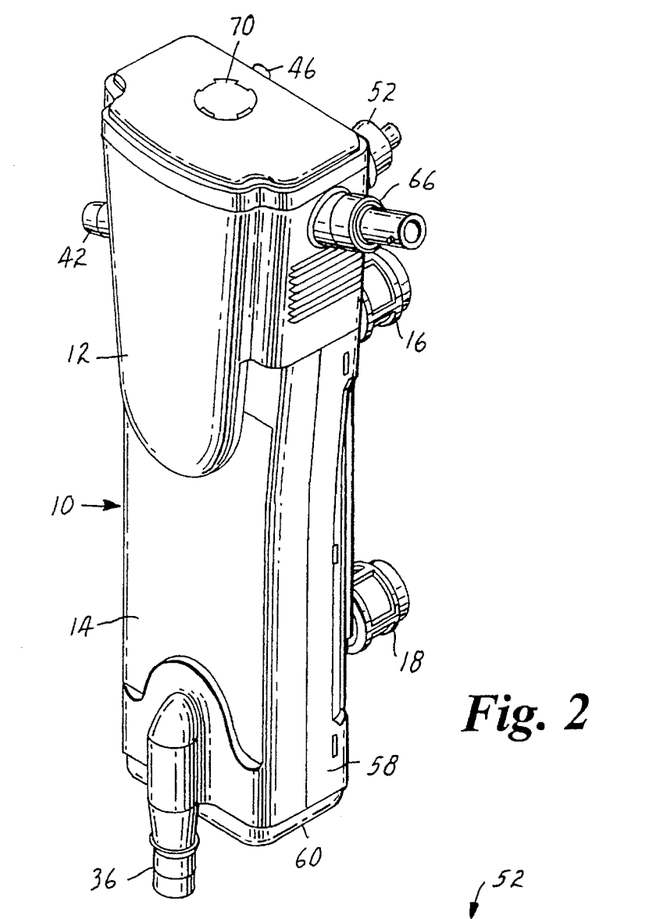
FIG. 2 is a perspective view of a cardioplegia delivery device with an integrated heat exchanger for use in cold cardioplegia delivery.

The cardioplegia delivery system of the present invention can be understood generally with reference to FIG. 1. The cardioplegia delivery system includes cardioplegia delivery device 10 which, in this embodiment includes an air chamber 12 and a heat exchanger 14. Cardioplegia delivery device 10 will be discussed in more detail with respect to FIGS. 2–7. In this embodiment heat exchanger 14 is incorporated with air chamber 12 into a single integral unit. Heat exchanger 14 and air chamber 12 may be bonded or affixed together in any conventional manner resulting in a fluid tight seal. Heat exchanger 14 includes an inlet 16 and an outlet 18 which, in operation, are connected to a source of heat exchange fluids (not shown) such as cold water. Although the embodiment of the cardioplegia delivery device 10 illustrated in FIG. 1 includes heat exchanger 14 the system shown may also be used with the cardioplegia delivery device shown in FIGS. 8–10 which is used for warm cardioplegia and does not include a heat exchanger.

The cardioplegia delivery system of FIG. 1 includes at least one cardioplegia solution source 20. In the embodiment disclosed two cardioplegia solution sources 20 are used. The sources may contain identical cardioplegia solution or one source may contain a cardioplegia solution having a higher concentration of potassium than the other. The higher concentration may be used initially with the lower concentration source being used after the heart has been arrested. Shunts 22 and 24 are used to select which of the solution sources 20 are used. The perfusionist may allow cardioplegia solution to flow through solution line 28 by opening shunt 30. Oxygenator 26 provides a source of oxygenated blood which is pumped through blood line 32 by roller pump 34 to the inlet 36 of cardioplegia delivery device 10. The delivery circuit may be provided with a shunt 38 which allows the perfusionist to supply pure blood to the cardioplegia delivery device 10.

Figure 4:
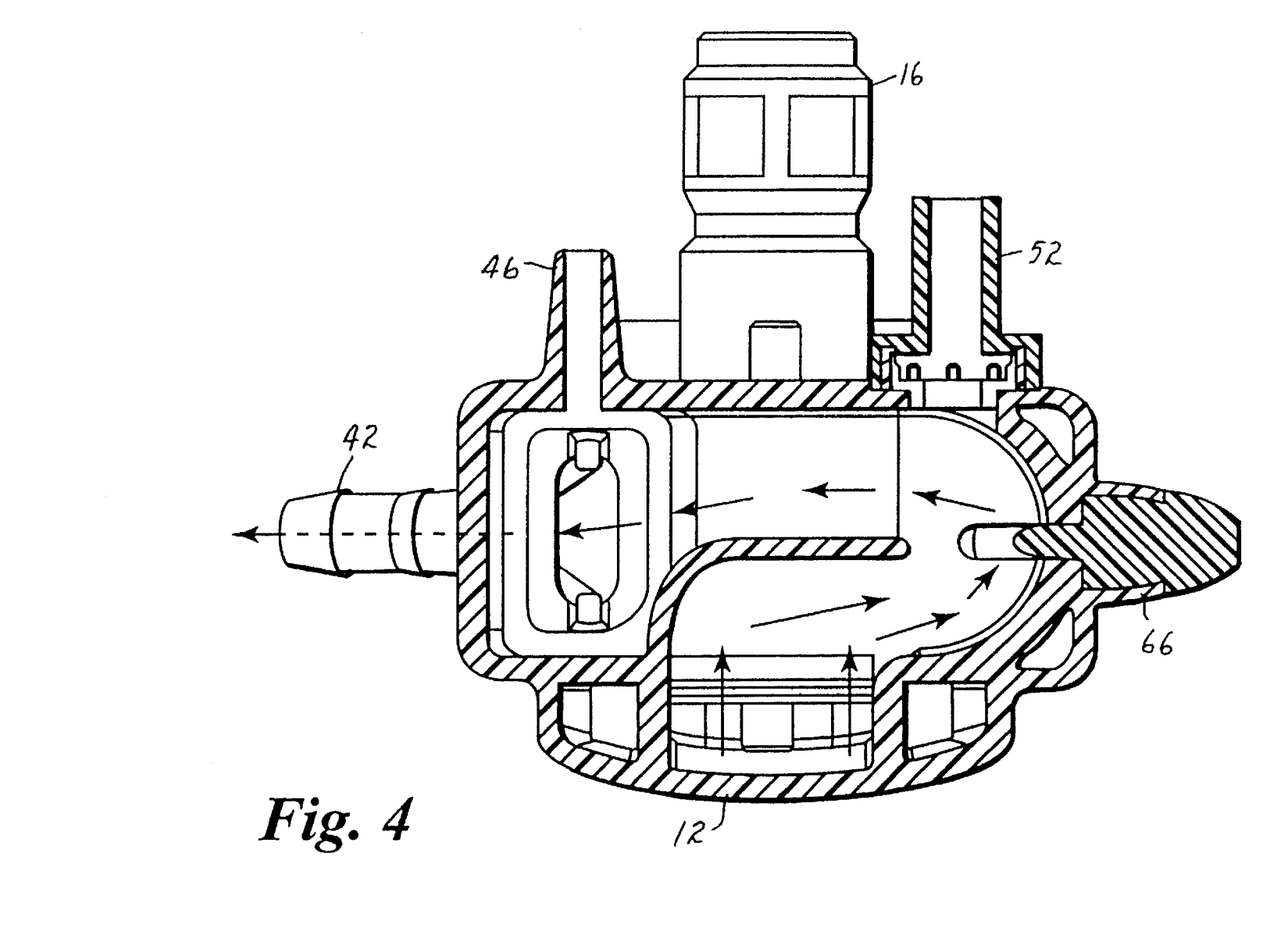
FIG. 4 is a top view in cross-section of the cardioplegia delivery device of FIG. 2 illustrating the cardioplegia fluid flow path.

Depending upon the size of the tubing and the activation of the various shunts in the delivery circuit the perfusionist is able to supply cardioplegia fluid to the inlet 36 of delivery device 10 in varying mixtures. It will be apparent that as the cardioplegia solution and blood are pumped through pump 34 they are mixed at a Y connection 40 prior to entering inlet 36 through cardioplegia fluid line 41. The cardioplegia fluid passes through heat exchanger 14 and air chamber 12 and exits the device through an outlet port 42 as better seen in FIG. 2. Outlet port 42 is connected to a patient return line 44 through which the cardioplegia fluid is delivered for perfusion of the patient's heart. Air chamber 12 includes a pressure monitor port 46 (as best seen in FIG. 4) which may be connected to a pressure transducer 48 for display of the internal pressure of the air chamber at pressure gauge 50.

Air chamber 12 also includes a pressure relief valve 52 as best seen in FIGS. 3–6. Pressure relief valve 52 is connected by tubing 54 to a cardiotomy reservoir 56. As will be discussed in more detail hereafter this allows cardioplegia fluid to be recirculated back to the cardiotomy reservoir if the internal pressure of the system exceeds a predetermined level.

Cold Cardioplegia Delivery Device

Figure 3:
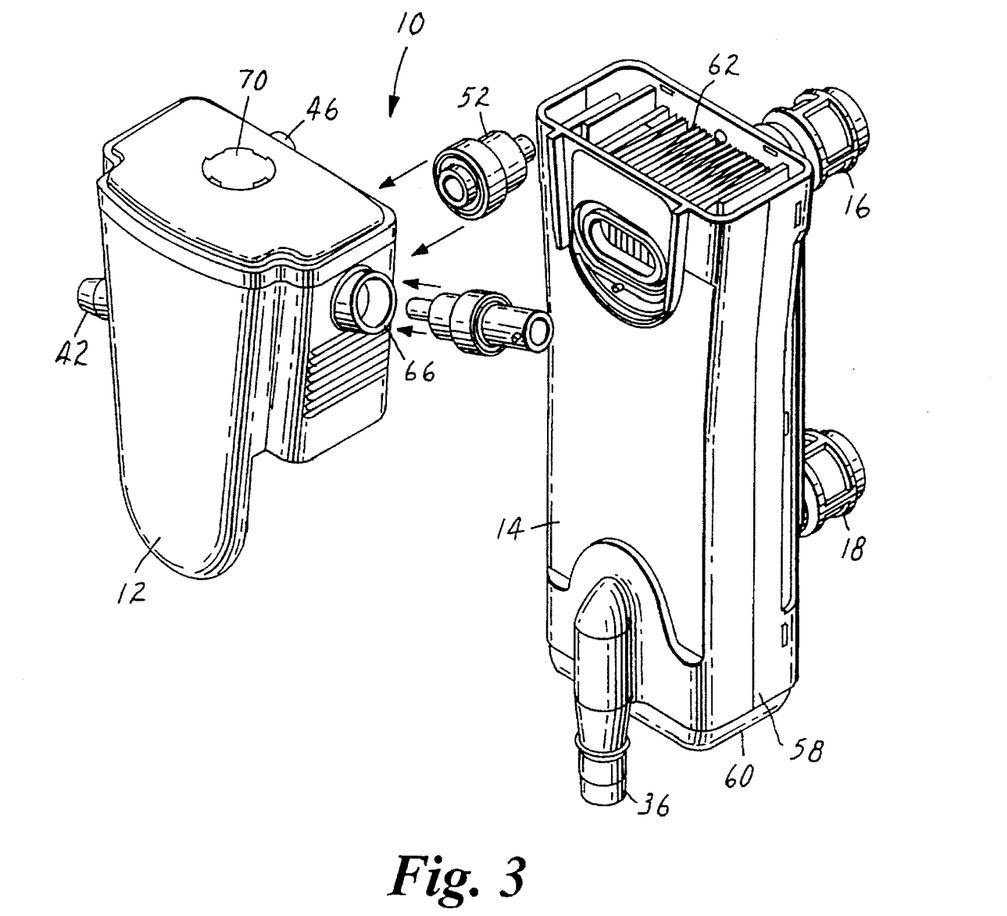
FIG. 3 is an exploded view of the cardioplegia delivery device of FIG. 2.

The cold cardioplegia delivery device 10 shown in FIG. 1 is set forth in more detail in FIGS. 2–7. As best seen in FIG. 3 device 10 comprises two distinct components, air chamber 12 and heat exchanger 14. Heat exchanger 14 includes a heat exchanger housing 58 and an end cap 60. A pleated heat exchange element 62 is contained within housing 58. Element 62 is comprised of a chevron-grooved, closely packed, pleated stainless steel sheet bent in an accordion fashion to create separate vertical channels. Cardioplegia fluid flows through the channels on one side of the stainless steel sheet while heat exchange fluid, typically water, is pumped into the unit through inlet 16, through the channels on the other side of heat exchange element 62 and out of the heat exchanger through outlet 18. By controlling the temperature of the water, one is able to control (heat or cool) the temperature of the cardioplegia fluid. The finned arrangement of the heat exchanger is designed to channel blood into a thin film for gentle mixing and efficient heat exchange yet allowing for ease of priming the unit without trapping air.

Figure 7:
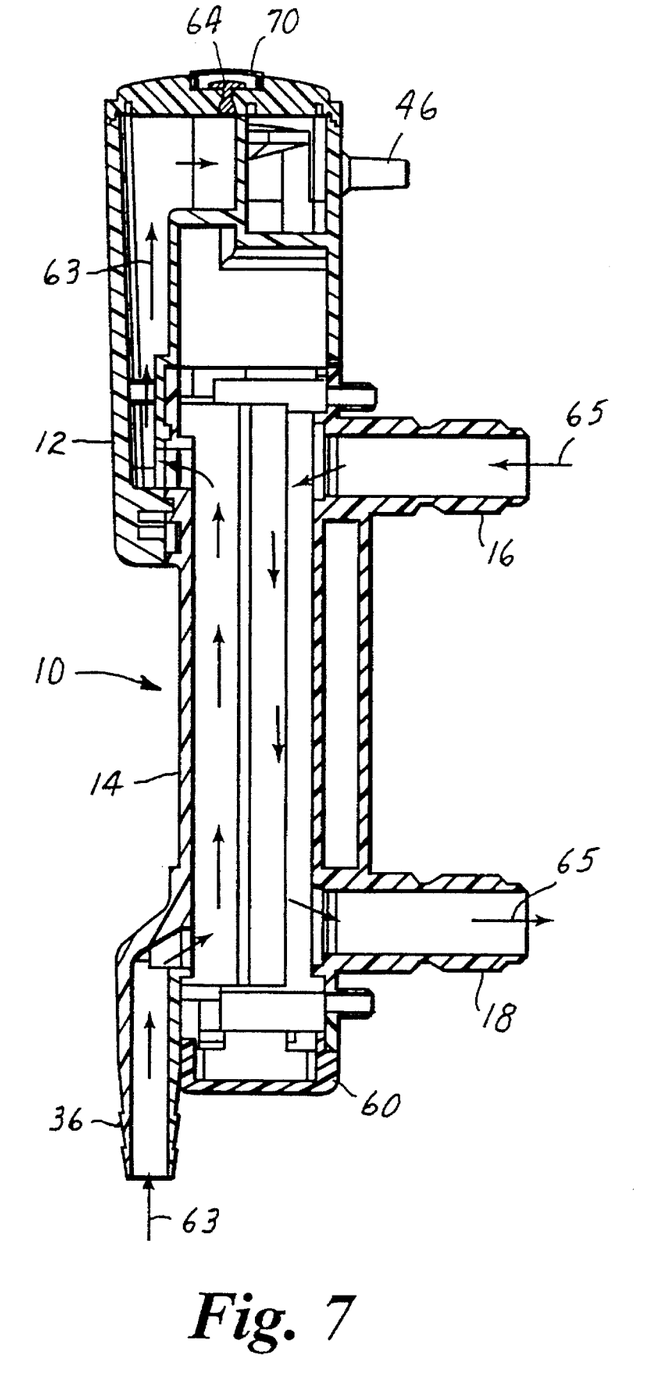
FIG. 7 is a cross-sectional side view of the cardioplegia delivery device of FIG. 2 showing the flow paths of the cardioplegia fluid and heat exchange fluid.

The flow paths of cardioplegia fluid (arrows 63) and water (arrows 65) through the heat exchanger are illustrated in FIG. 7. The flow paths are counter current thus providing for greater heat exchange efficiency. The flow paths on either side of the pleated fins are bounded at the top and bottom by potting material. The unit is constructed so that the fins extend through the potting material on both the top and bottom of the unit reducing the possibility of a water to cardioplegia fluid leak. Any fluid leaking through the potting material will leak to the atmosphere instead of the other side of the fin.

Figure 5:
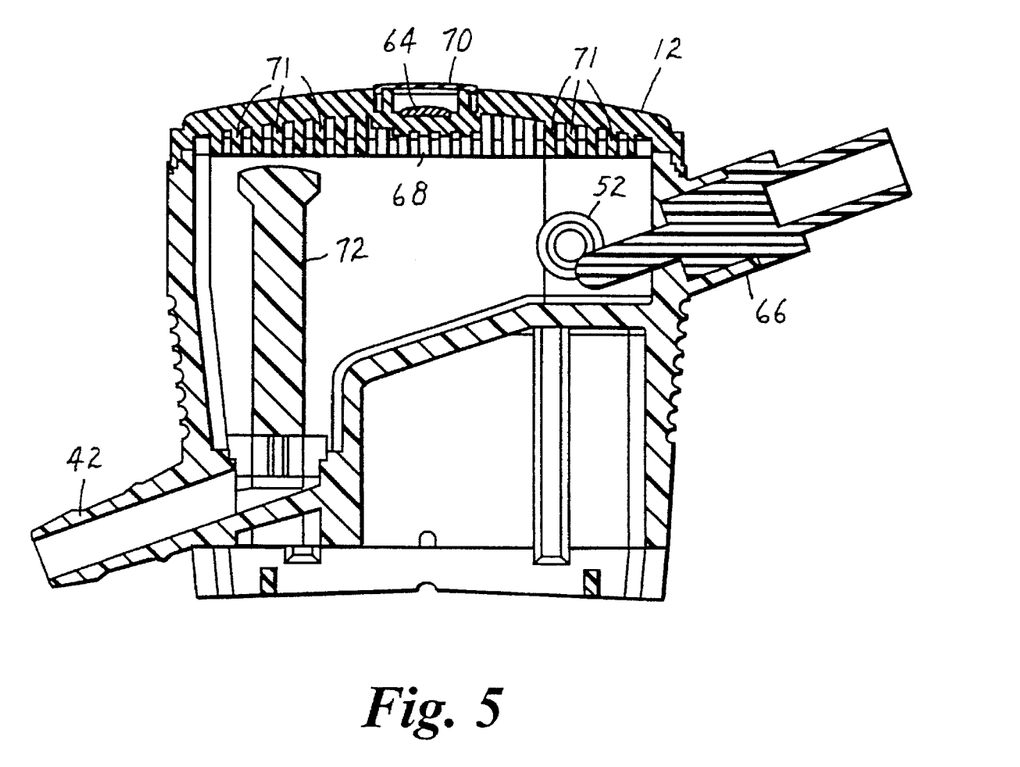
FIG. 5 is a cross-sectional view of the air chamber portion of the cardioplegia delivery device of FIG. 3.

Air chamber 12 includes a one-way air elimination valve 64 and a temperature port 66 as best seen in FIG. 5. Air chamber 12 includes a membrane 68 positioned above the fluid level in the air chamber. In the preferred embodiment membrane 68 is comprised of a hydrophobic PTFE material with a pore size of 0.45 microns, a thickness of 0.01 cm and a surface area of 4.1 cm$^2$. Such a membrane will pass air but not fluids up to a pressure of 1300 mmHg. This is known as the water entry pressure of the membrane. Membrane 68 is supported by a plurality of support struts 71 which hold the membrane in place and prevent the shape of the membrane from distorting under pressure. Valve 64 prevents air from flowing back across the membrane into the cardioplegia fluid path in the event a negative pressure were created inside the air chamber. Valve 64 is a one-way umbrella check valve. In the preferred embodiment, valve 64 is comprised of silicone rubber and will release internal air pressure when it reaches 5 mmHg. The valve reseals when the internal pressure falls below 3 mmHg thus preventing outside air from flowing back into the air chamber. The one-way valve 64 is protected on top of the device with a vented plastic cover 70.

To further enhance the air elimination capacity of air chamber 12 a bubble screen 72 is included. Screen 72 is positioned in the cardioplegia fluid flow path just above the cardioplegia fluid outlet 42. Screen 72 serves two useful purposes. First, it deflects air bubbles in the cardioplegia fluid to the top of the air chamber where they can be eliminated across membrane 68. Second, the screen functions as a filter to remove solid particulate from the cardioplegia fluid before it is delivered to the patient's heart. In the preferred embodiment the screen is comprised of a 105 micron polyester mesh molded into a support structure of ABS plastic.

Figure 6:
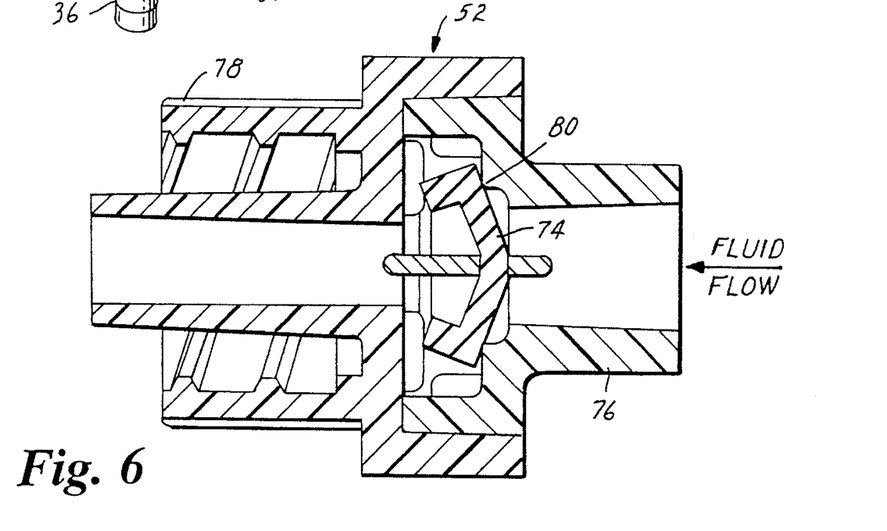
FIG. 6 is an enlarged cross-sectional view of the pressure relief valve utilized in the present invention.

Potential over pressurization of the device is prevented by pressure relief valve 52 which is mounted in the housing of air chamber 12. The specific construction of pressure relief valve is illustrated in FIG. 6. Valve 52 can be seen to comprise a molded disk cup 74 held between back housing 76 and front housing 78. Back housing 76 is securely fixed as by bonding or by other suitable means to air chamber 12 so that valve 52 is held securely in place. Under normal operating conditions disk 74 rests against disk seat 80 preventing the flow of fluid from the air chamber. However, the pressure relief valve 52 is designed to open to relieve internal pressure when the internal pressure rises significantly above normal operating pressure. For example, the pressure relief valve may be designed to open at approximately 600 mmHg or at such other pressure that is selected to protect the patient and system components. When the pressure in the air chamber exceeds 600 mmHg the valve opens to divert fluid until the internal pressure falls to below 600 mmHg, at which time the molded disk cup 74 reseats and stops the flow of fluid. Pressure relief valve 52 eliminates the potential of rupturing the device or other circuit components or of reaching the water entry pressure of membrane 68. It should be appreciated that although a specific configuration has been illustrated for valve 52 other known valve configurations could be utilized within the scope of the present invention. Additionally, it is possible to select valves or valve material which will cause the valve to open at different internal pressures depending on the specific design criteria used.

Warm Cardioplegia

Figure 8:
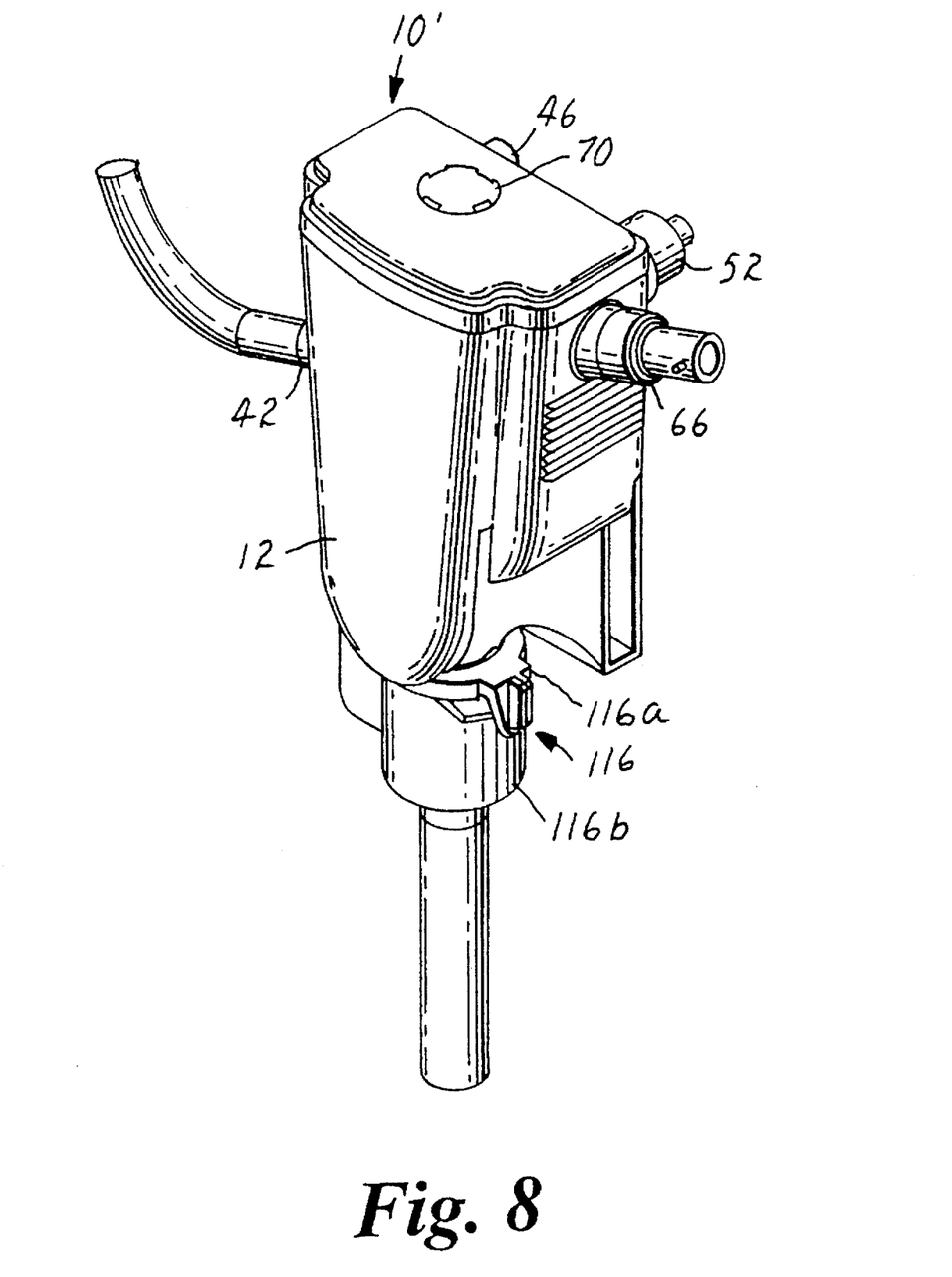
FIG. 8 is a perspective view of a cardioplegia delivery device utilized in the administration of warm cardioplegia.
Figure 9:
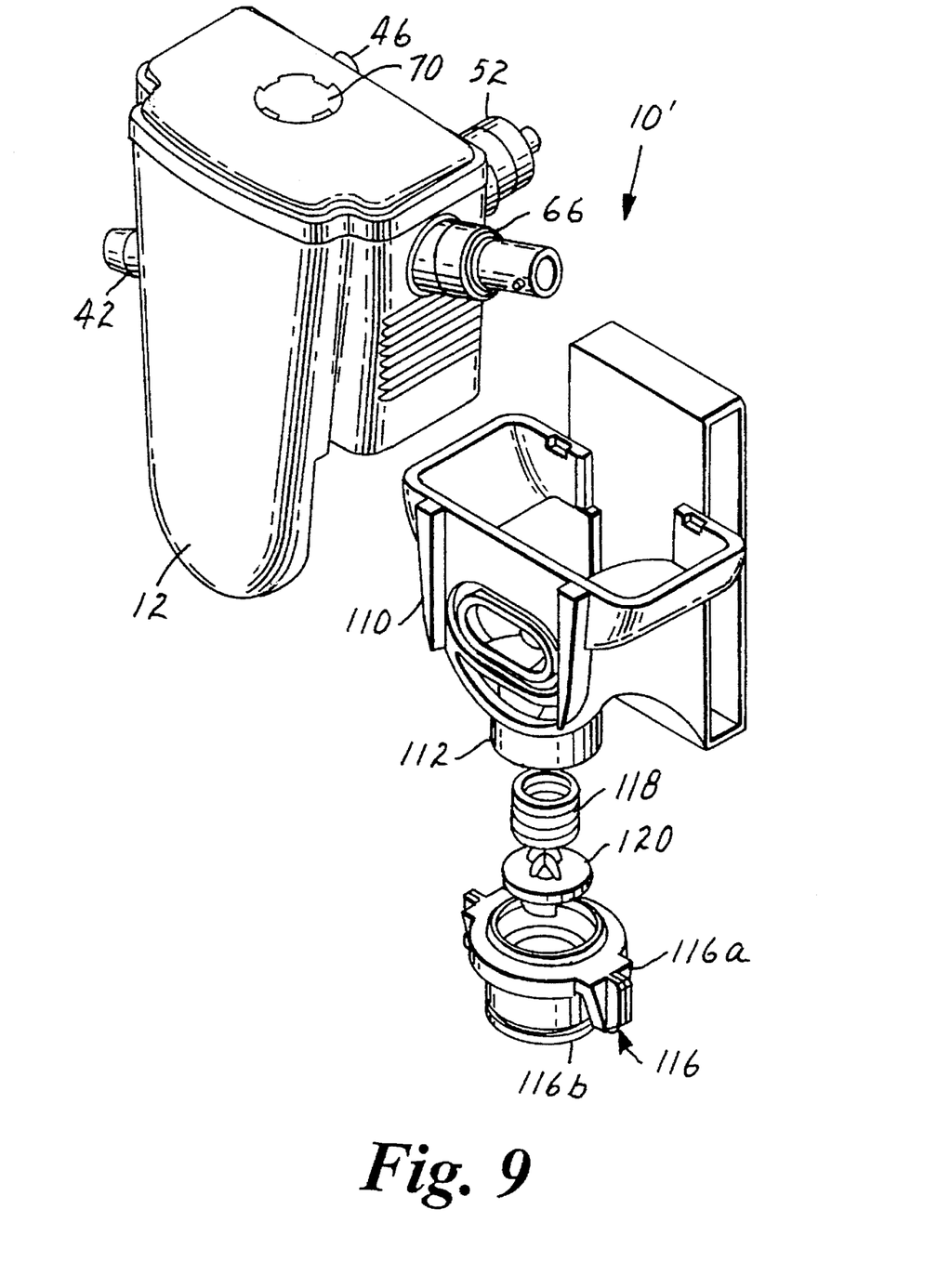
FIG. 9 is an exploded view of the cardioplegia delivery device of FIG. 8.
Figure 10A:
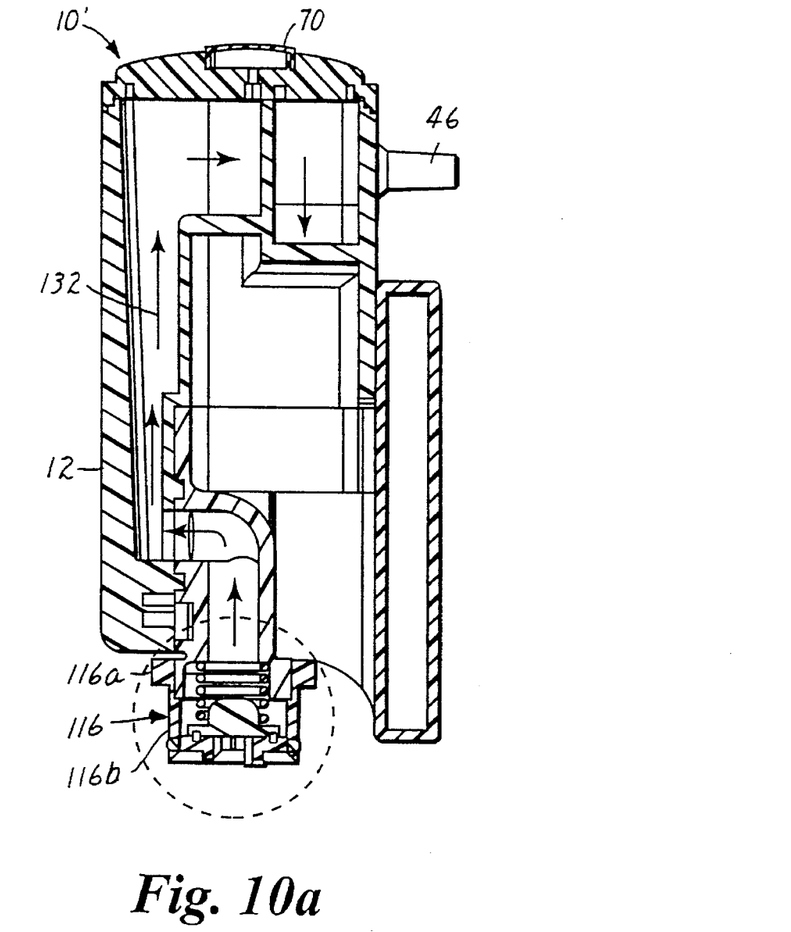
FIG. 10a is a cross-sectional side view of the cardioplegia delivery device of FIG. 8 illustrating the flow path of cardioplegia fluid and FIG. 10b is a magnified view in cross-section of the inlet of the delivery device.
Figure 10B:
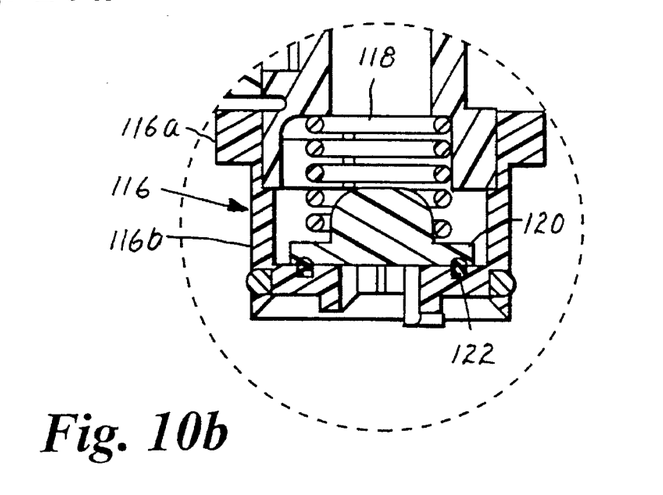

As previously mentioned, the cardioplegia delivery device 10 shown in FIG. 1 may include a heat exchanger (as shown) for cold cardioplegia delivery or it may consist of a device having no heat exchanger when warm cardioplegia is desired. Such a warm cardioplegia delivery device is shown in FIGS. 8–10. Cardioplegia delivery device 10' utilizes an air chamber which is identical to that utilized in the cold cardioplegia device described previously and, for purposes of clarity, like reference numerals will be used to identify the air chamber of the warm cardioplegia delivery device and its components.

As shown in FIG. 9 warm cardioplegia delivery device 10' is comprised of air chamber 12 which is securely bonded to a warm unit adapter 110. Warm unit adapter 110 includes an inlet into which the upper portion 116a of a valved disconnect 116 is attached. Upper portion 116a includes a spring 118 and a shut off valve 120. As best seen in FIG. 10a, when the upper portion 116a of disconnect 116 is not locked into position with the lower portion 116b, the base of shut off valve 120 is seated against O-ring 122 which blocks the flow of fluids through the disconnect. Conversely, when the upper and lower portions are locked together, valves in both portions open to allow fluid flow through delivery device 10.

Warm cardioplegia delivery device 10' is used when warm cardioplegia is desired. The method of use is identical to that described in connection with FIG. 1 except that no heat exchanger is provided to either cool or heat the cardioplegia fluid. The flow of cardioplegia fluid through warm cardioplegia delivery device 10' is shown in FIG. 10a by arrows 132.

From the foregoing detailed description of specific embodiments of the invention, it should be apparent that an improved cardioplegia delivery device has been disclosed herein in detail. This has been done for the purpose of illustration only, and is not intended to be limiting with respect to the scope of the appended claims, which follow. In particular, it is contemplated by the inventors that various substitutions, alterations and modifications may be made to the embodiments of the invention without departing from the spirit and scope of the invention as defined by the claims. For instance, the choice of materials or variations in the shape or the type of various individual components are believed to be a matter of routine for a person of ordinary skill in the art with knowledge of the embodiments disclosed herein.

We claim:

1. A blood cardioplegia delivery device comprising:

a housing having a fluid inlet port adapted to receive a cardioplegia fluid comprising one of blood, a mixture of blood and cardioplegia solution, and cardioplegia solution, and having a fluid outlet port in fluid communication with the fluid inlet port;

an air removal element located within the housing; and a pressure relief valve incorporated into the housing, the pressure relief valve being adapted to divert fluid flow if the fluid pressure in an interior portion of the housing exceeds a selected fluid pressure.

2. A blood cardioplegia delivery device comprising:

a housing having a fluid inlet port adapted to receive a cardioplegia fluid comprising one of blood, a mixture of blood and cardioplegia solution, and cardioplegia solution, and having a fluid outlet port in fluid communication with the fluid inlet port;

an air removal element located within the housing, the air removal element having a membrane and a one-way valve adapted to allow air to flow from the housing through the membrane to the exterior of the housing when the air pressure in the air chamber exceeds a selected air pressure ; and a pressure relief valve incorporated into the housing, the pressure relief valve being adapted to divert fluid flow if the fluid pressure in an interior portion of the housing exceeds a selected fluid pressure.

3. The cardioplegia delivery device of claim 2 wherein the air removal element further comprises a screen positioned between the fluid inlet and the fluid outlet.

4. A blood cardioplegia delivery device comprising:

a housing having a fluid inlet port adapted to receive a cardioplegia fluid comprising one of blood, a mixture of blood and cardioplegia solution, and cardioplegia solution, and having a fluid outlet port in fluid communication with the fluid inlet port;

an air removal element located within the housing;

a pressure relief valve incorporated into the housing, the pressure relief valve being adapted to divert fluid flow if the fluid pressure in an interior portion of the housing exceeds a selected fluid pressure; and a heat exchanger having a heat exchange fluid flow path between a heat exchange fluid inlet and a heat exchange fluid outlet and having a cardioplegia fluid flow path between a cardioplegia fluid inlet and a cardioplegia fluid outlet, the cardioplegia fluid outlet of the heat exchanger being connected to the fluid inlet port of the housing.

5. The cardioplegia delivery device of claim 2 wherein the membrane is adapted to allow air to flow through the membrane and to block fluid from flowing through the membrane under normal operating pressures of the device.

6. A blood cardioplegia delivery device comprising:

an air chamber having a housing defining an interior portion and having a fluid inlet port adapted to receive a cardioplegia fluid comprising one of blood, a mixture of blood and cardioplegia solution, and a cardioplegia solution, the housing further having a fluid outlet adapted for delivery of the cardioplegia fluid to a patient;

a membrane located in the air chamber;

a one-way valve located in the housing near the membrane, the one-way valve adapted to allow airflow from the air chamber through the membrane to the exterior of the housing when the air pressure in the air chamber rises above a predetermined air pressure;

a pressure relief valve incorporated into the housing and adapted to open so that cardioplegia fluid flows through the pressure relief valve when the fluid pressure in the interior portion of the housing rises above a predetermined fluid pressure; and a heat exchanger connected to the housing of the air chamber.

7. The cardioplegia delivery device of claim 6 further comprising a screen positioned within the housing between the fluid inlet and the fluid outlet.

8. The cardioplegia delivery device of claim 6 wherein the predetermined air pressure is 5 mmHg.

9. The cardioplegia delivery device of claim 6 wherein the predetermined fluid pressure is 600 mmHg.

10. A method of delivering cardioplegia fluid including blood, a mixture of blood and cardioplegia solution, or cardioplegia solution, to the heart of a patient during open heart surgery, the method comprising:

providing an air chamber having a housing including a fluid inlet port adapted to receive the cardioplegia fluid and having a fluid outlet port in fluid communication with the fluid inlet port, the air chamber further having an air removal element located within the housing and a pressure relief valve incorporated into the housing, the pressure relief valve being adapted to divert fluid flow from the housing if the fluid pressure in the housing exceeds a selected fluid pressure;

connecting the fluid inlet port of the air chamber to a cardioplegia fluid source;

connecting the fluid outlet port of the air chamber to cardioplegia tubing connected for infusion of the cardioplegia fluid to the heart of the patient; and delivering the cardioplegia fluid from the cardioplegia source through the air chamber to the patient's heart.

11. The method of claim 10 wherein the step of providing comprises providing an air removal element that includes a membrane and a one-way valve adapted to allow air to flow from the air chamber through the membrane to the exterior of the housing when the air pressure in the air chamber exceeds a selected air pressure.

12. The method of claim 11 wherein the providing step includes providing an air removal element that further includes a screen positioned between the fluid inlet and the fluid outlet.

13. The method of claim 10 further including adjusting the temperature of the cardioplegia fluid that is delivered to the patient's heart.

* * * * *

UNITED STATES PATENT AND TRADEMARK OFFICE
CERTIFICATE OF CORRECTION

PATENT NO. : 5,609,571
DATED : March 11, 1997
INVENTOR(S) : Buckberg et al.

It is certified that error appears in the above-identified patent and that said Letters Patent is hereby corrected as shown below:

Column 1, line 15, replace "deuce" with --device--; line 32, replace "hear" with --heart--; line 33, replace "hear" with --heart--.

Signed and Sealed this

Twenty-fifth Day of April, 2000

*Attest:*

Q. TODD DICKINSON

*Attesting Officer*     *Director of Patents and Trademarks*